United States Patent
Tin et al.

(10) Patent No.: US 9,157,855 B2
(45) Date of Patent: Oct. 13, 2015

(54) MATERIAL CLASSIFICATION

(71) Applicant: CANON KABUSHIKI KAISHA, Tokyo (JP)

(72) Inventors: Siu-Kei Tin, Milpitas, CA (US); Francisco Imai, Mountain View, CA (US)

(73) Assignee: CANON KABUSHIKI KAISHA, Tokyo (JP)

( * ) Notice: Subject to any disclaimer, the term of this patent is extended or adjusted under 35 U.S.C. 154(b) by 126 days.

(21) Appl. No.: 14/020,515

(22) Filed: Sep. 6, 2013

(65) Prior Publication Data
US 2015/0070703 A1    Mar. 12, 2015

(51) Int. Cl.
| | |
|---|---|
| *G01N 21/55* | (2014.01) |
| *G01N 21/47* | (2006.01) |
| *B07C 5/28* | (2006.01) |
| *B07C 5/34* | (2006.01) |
| *B07C 5/342* | (2006.01) |
| *B07C 5/00* | (2006.01) |
| *G01N 21/84* | (2006.01) |

(52) U.S. Cl.
CPC ........ *G01N 21/55* (2013.01); *B07C 5/00* (2013.01); *B07C 5/28* (2013.01); *B07C 5/34* (2013.01); *B07C 5/342* (2013.01); *G01N 21/84* (2013.01); *G01N 2021/845* (2013.01)

(58) Field of Classification Search
USPC ............ 356/392–394, 73, 445; 382/101, 173, 382/306; 209/900, 583, 584, 581, 587
See application file for complete search history.

(56) References Cited

U.S. PATENT DOCUMENTS

| | | | | |
|---|---|---|---|---|
| 3,747,755 | A * | 7/1973 | Senturia et al. | 209/559 |
| 4,260,062 | A * | 4/1981 | Lockett | 209/582 |
| 4,369,886 | A * | 1/1983 | Lane et al. | 209/564 |
| 4,586,613 | A * | 5/1986 | Horii | 209/556 |
| 5,134,291 | A * | 7/1992 | Ruhl et al. | 250/339.11 |

(Continued)

OTHER PUBLICATIONS

Kuncheva, Ludmila I., "Combining Pattern Classifiers, Methods and Algorithms", Wiley-Interscience, 2004.

(Continued)

*Primary Examiner* — Sang Nguyen
(74) *Attorney, Agent, or Firm* — Fitzpatrick, Cella, Harper & Scinto

(57) ABSTRACT

The present disclosure relates to classification of a material type of an unknown material. The material type is classified into a probability distribution of multiple predetermined material types by using a collection of plural predetermined material classifiers. Each material type of the multiple predetermined material types is associated with a corresponding best performing classifier from the collection of plural predetermined material classifiers by a predesignated stored association. The plural material classifiers are applied to the unknown material to obtain a list of candidate material types. A list of potential best performing classifiers is looked up using the list of candidate material types as a reference into the predesignated stored association. A respective probability that the unknown material belongs to a material type is assigned based on the list of potential best performing classifiers.

39 Claims, 8 Drawing Sheets

(56) References Cited

U.S. PATENT DOCUMENTS

| | | | | |
|---|---|---|---|---|
| 5,533,628 | A * | 7/1996 | Tao | 209/580 |
| 5,870,204 | A * | 2/1999 | Chiu et al. | 356/430 |
| 5,884,775 | A * | 3/1999 | Campbell | 209/581 |
| 5,917,585 | A * | 6/1999 | Roe et al. | 356/73 |
| 6,728,391 | B1 * | 4/2004 | Wu et al. | 382/101 |
| 7,024,033 | B2 | 4/2006 | Li et al. | |
| 7,763,820 | B1 * | 7/2010 | Sommer et al. | 209/576 |
| 7,840,061 | B2 | 11/2010 | Porikli et al. | |
| 8,015,132 | B2 | 9/2011 | Xu | |
| 8,233,704 | B2 | 7/2012 | Han et al. | |
| 2007/0278139 | A1 * | 12/2007 | Cowling et al. | 209/606 |
| 2013/0126399 | A1 * | 5/2013 | Wolff | 209/555 |

OTHER PUBLICATIONS

Alvarez et al., "Texton Theory Revisited: A Bag-Of-Words Approach to Combine Textons", Pattern Recognition, vol. 45, Issue 12, Dec. 2012, pp. 4312-4325.

Wu et al., "Optimizing Discrimination-Efficiency Tradeoff in Integrating Heterogeneous Local Features for Object Detection", University of Southern California, Institute for Robotics and Intelligent Systems, 2008, 8 pages.

Woods et al., "Combination of Multiple Classifiers Using Local Accuracy Estimates", IEEE Transactions on Pattern Analysis and Machine Intelligence, vol. 19, No. 4, Apr. 1997, pp. 405-410.

Todorovski et al., "Combining Classifiers with Meta Decision Trees", Machine Learning, 50, 2003, pp. 223-249.

* cited by examiner

MATERIAL CLASSIFICATION

FIELD

The present disclosure relates to the classification of materials, and more particularly relates to the classification of materials by combining different material classifiers.

BACKGROUND

In the field of material classification, a material classifier is used to classify an unknown material into one of multiple material types. A material classifier is typically based on a physical property used to differentiate different material types.

SUMMARY

Several approaches have been considered for identification of a material type. For example, a classifier based on a spectral approach has been considered in cases where a material has a distinctive spectral signature. A spectral approach may be considered in situations where color is an important feature of the material, or in situations where appearance of the material is the same from every viewing angle, such as a Lambertian material.

As another example, a classifier based on a texture approach has been considered in cases where materials have a distinctive texture, such as wood or textile. Such an approach considers a bidirectional texture function (BTF), which provides a comprehensive description of the texture of a material.

In some approaches, a bidirectional reflectance distribution function (BRDF) has been considered for use in situations where the appearance of the material depends on the angle of viewing (e.g., due to reflection of light), such as when the material is a metal.

In other approaches, a bidirectional surface scattering reflectance distribution function (BSSRDF) has been considered for use when the material exhibits significant subsurface scattering, such as plastic material or other translucent materials.

In some examples, a classifier based on some of the above approaches may be implemented using an "active light" method, such as a structured light method and/or a laser speckle method, with an additional light source such as a projector or a laser. In other examples, a classifier based on some of the above approaches may be implemented using a "passive light" method, i.e., using only existing light without an additional light source.

By using one of the approaches discussed above, efforts have been made to classify or identify a material in order to accurately determine the material type.

Efforts have also been made to combine a color approach with a texture approach, in an attempt to build a more discriminative classifier. See, for example, S. Alvarez et al., *Texton theory revisited: A bag-of-words approach to combine textons*, Pattern Recognition, Volume 45, Issue 12, pp. 4312-4325. However, the inventors herein have found that conventional attempts at combining classifiers are unsophisticated and/or fixed, since such attempts are often based on a specific internal implementation of each classifier. In addition, conventional classifiers often rely heavily on a training process that uses training data, for which the process of training, or learning, takes time.

The foregoing situation is addressed herein by combining pre-existing classifiers based on different approaches, usually without a priori knowledge of the details and/or algorithms of the pre-existing classifiers and without relying on training data, in order to classify a material.

Thus, in an example embodiment described herein, a material type of an unknown material is classified into a probability distribution of multiple predetermined material types by using a collection of plural predetermined material classifiers, where each material type of the multiple predetermined material types is associated with a corresponding best performing classifier from the collection of plural predetermined material classifiers by a predesignated stored association. The plural material classifiers are applied to the unknown material to obtain a list of candidate material types, and a list of potential best performing classifiers is looked up using the list of candidate material types as a reference into the predesignated stored association. A respective probability that the unknown material belongs to a material type is assigned based on the list of potential best performing classifiers.

By virtue of performing material classification using predesignated stored associations, it is typically possible to more accurately classify a material by combining predetermined material classifiers, without having specific information about the implementation of the predetermined material classifiers. Moreover, it is ordinarily possible to combine predetermined material classifiers without relying on data used in the training of the predetermined classifiers. In this way, it is typically possible to avoid situations in which training data is no longer available for reference, and to avoid situations in which different classifiers have been trained using different sets of data that might not be compatible. Furthermore, training data often may not include data seen during deployment, such that a classifier trained from such data may make incorrect predictions. Therefore, classifying a material type without requiring a learning process reduces dependence on unreliable or insufficient training data.

In addition, by way of background, training a classifier using training data conventionally requires increased processing time, such that it is difficult to dynamically combine classifiers. By virtue of the claimed arrangement, in which predesignated stored associations are used to perform material classification, it is typically possible to dynamically combine predetermined material classifiers. As such, the relative importance of each classifier can be easily changed by modifying the predesignated stored associations based on a specific set of circumstances. Furthermore, a new predetermined classifier can be easily added to the collection of classifiers. In this way, it is ordinarily possible to obtain feedback when classifying a material, in order to modify the predesignated stored associations and to leverage the advantages and disadvantages of each classifier to improve the classification process.

In an example embodiment also described herein, application of the plural material classifiers to the unknown material comprises obtaining one or more feature vectors for the unknown material and inputting a corresponding one of the feature vectors into each of the plural material classifiers so as to obtain an output representative of material type from each of the plural material classifiers.

In further aspects of some example embodiments, the output of each material classifier is indicative of a probability that the unknown material belongs to each material type. Additionally, in some example embodiments, the output of each material classifier identifies a candidate material type that the unknown material belongs to.

Moreover, in yet other aspects, the collection of plural material classifiers includes a classifier based on texture discrimination, and the corresponding feature vector for such classifier is representative of texture of the unknown material. Also, in some example embodiments, the collection of plural material classifiers includes a classifier based on a spectral signature, and the corresponding feature vector for such classifier is representative of spectral reflectance of the unknown material. In some example embodiments, the collection of plural material classifiers includes a classifier based on a bidirectional reflectance distribution function, and the corresponding feature vector for such classifier is representative of an angular dependence of reflectance of the unknown material. In some other example embodiments, the collection of plural material classifiers includes a classifier based on a bidirectional surface scattering reflectance distribution function, and the corresponding feature vector for such classifier is representative of a subsurface scattering property of the unknown material.

According to aspects of some example embodiments, assignment of the respective probability that the unknown material belongs to a material type comprises determining a weight for each of the plural predetermined material classifiers by using the list of potential best performing classifiers, and assigning a respective probability that the unknown material belongs to a material type based on the weights of the plural predetermined material classifiers. According to some example embodiments, determining a weight for each of the plural predetermined material classifiers comprises a look up from a pre-computed table of weights. According to an aspect of some example embodiments, determining a weight for each of the plural predetermined material classifiers comprises use of a state machine that describes the behavior of the plural predetermined material classifiers, and finding a limit cycle of the state machine. According to another aspect of some example embodiments, assigning a respective probability that the unknown material belongs to a material type based on the weights of the plural predetermined material classifiers comprises calculating a weighted combination of the plural predetermined material classifiers using the weights.

In one example embodiment, the predesignated stored association by which each material type is associated with a corresponding best performing classifier is based on empirical data from labeled test samples. In some example embodiments, the predesignated stored association by which each material type is associated with a corresponding best performing classifier is based on theoretical behavior of the classifiers on the material types. According to an aspect of some example embodiments, the predesignated stored association by which each material type is associated with a corresponding best performing classifier is stored in a look up table.

According to some example embodiments, the multiple predetermined material types include a plastic type. In addition, in some example embodiments, the multiple predetermined material types include a metal type. In some further example embodiments, the multiple predetermined material types include a fabric type.

According to one example embodiment, a numerical count of the multiple predetermined material types is countably small.

According to some example embodiments, a candidate material type identity is provided for the unknown material based on the assigned probabilities of the material types.

This brief summary has been provided so that the nature of this disclosure may be understood quickly. A more complete understanding can be obtained by reference to the following detailed description and to the attached drawings.

DETAILED DESCRIPTION

Figure 1:
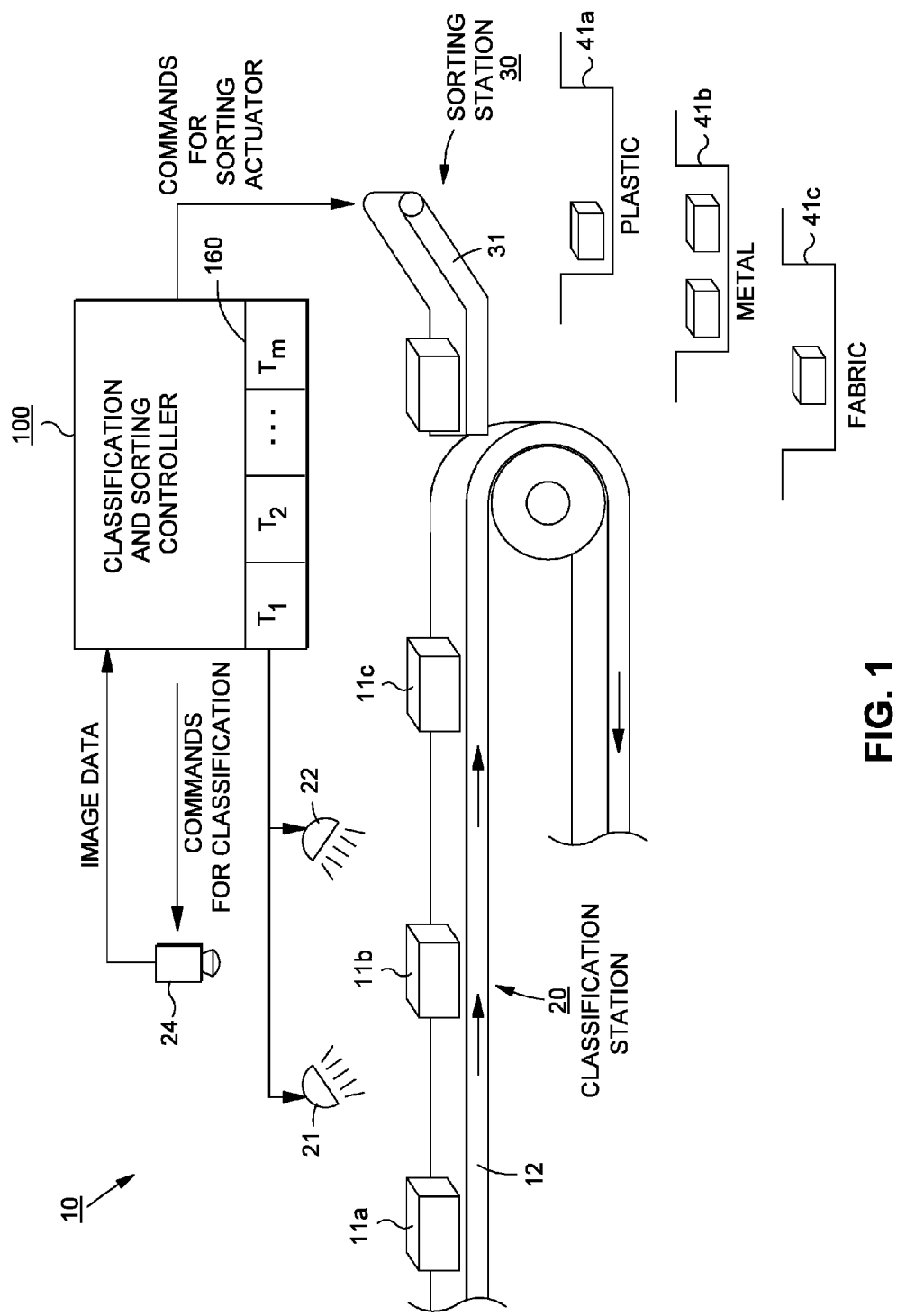
FIG. 1 is an example embodiment of a classification system according to the description herein, in the form of a recycling system in which objects to be recycled are classified according to the materials from which the objects are fabricated, and the classified objects are sorted for recycling according to their material classification.

FIG. 1 is an example embodiment of a classification system according to the description herein, in the form of a recycling system 10 in which objects to be recycled are classified according to the materials from which the objects are fabricated, and the classified objects are sorted for recycling according to their material classification.

While FIG. 1 depicts a recycling and/or sorting environment, it should be understood that this is simply an example environment in which the disclosure may be practiced, and that other environments or embodiments are of course possible. For example, material classification could also be used in the context of manufacturing, quality control, image retrieval and security, among many others.

As shown in FIG. 1, objects 11a, 11b, etc. are conveyed on a conveyor mechanism 12 to a classification station 20, where the objects are classified according to their material, and thence to a sorting station 30, where the objects are sorted, re-routed, or otherwise processed according to their material classification or identification. It should be understood that conveyor mechanism 12 is simply an example mechanism for moving objects, and other mechanisms, such as other robotic mechanisms, may be employed. In addition, although FIG. 1 depicts three objects, any number of objects may appear on conveyor mechanism 12 at a time.

Classification station 20 includes plural light sources 21 and 22, together with an image capture device 24 for capturing images of objects positioned at classification station 20. In some example embodiments, an object at the classification station is illuminated individually by each of the plural light sources under control of classification and sorting controller 100, and image capture device 24 captures one or more images for each individual illumination. Under control of the classification and sorting controller 100, a classification is made for the material from which the object is fabricated, by using a collection of plural predetermined material classifiers $T_1, T_2, \ldots, T_m$ (160).

Conveyor mechanism 12 continues to convey the object to sorting station 30, where sorting actuator 31 sorts the objects according to the material classification. Sorting is controlled by classification and sorting controller 100, which commands actuator mechanism 31 to sort the classified objects into multiple receptacles 41a, 41b and 41b.

In this example embodiment, material classification differentiates between different types of materials from which the objects are fabricated, such as metal, plastic and fabric. Naturally, it will be understood that this is a non-limiting example. In other embodiments, material classification could differentiate between metals such as brass, copper and aluminum, between plastic and glass, between fabric and paper, between different types or colors of plastics and glass, and so forth, or between any and all of these. In addition, other embodiments might include a classification of "unknown", signifying that material classification did not succeed with confidence, with a corresponding receptacle for which manual sorting is required.

In FIG. 1, image capture device 24 is shown as a digital still camera or a digital video camera. It is understood, however, that the following description encompasses arbitrary arrangements which can incorporate or utilize imaging assemblies with capture optics, for instance, a data processing apparatus having an image sensing function (e.g., a personal computer) or a portable terminal having an image sensing function.

It should be also understood that controller 100 may be included in a computer, the computer generally comprising a programmable general purpose computer having an operating system, such as Microsoft® Windows® or Apple® Mac OS® or LINUX, and which is programmed as described below so as to perform particular functions and, in effect, become a special purpose computer when performing these functions.

In some embodiments, the computer may be a mobile computer. In addition, computing equipment for practicing aspects of the present disclosure can be implemented in a variety of embodiments. For example, in some embodiments, the functionality of controller 100 may be incorporated into image capture device 24. In other embodiments, the computer may comprise, for example, a desktop computer or a computing cluster, or may include an imaging device instead of communicating with a separate image capture device 24. Other embodiments are possible according to the application and environment.

Figure 2:
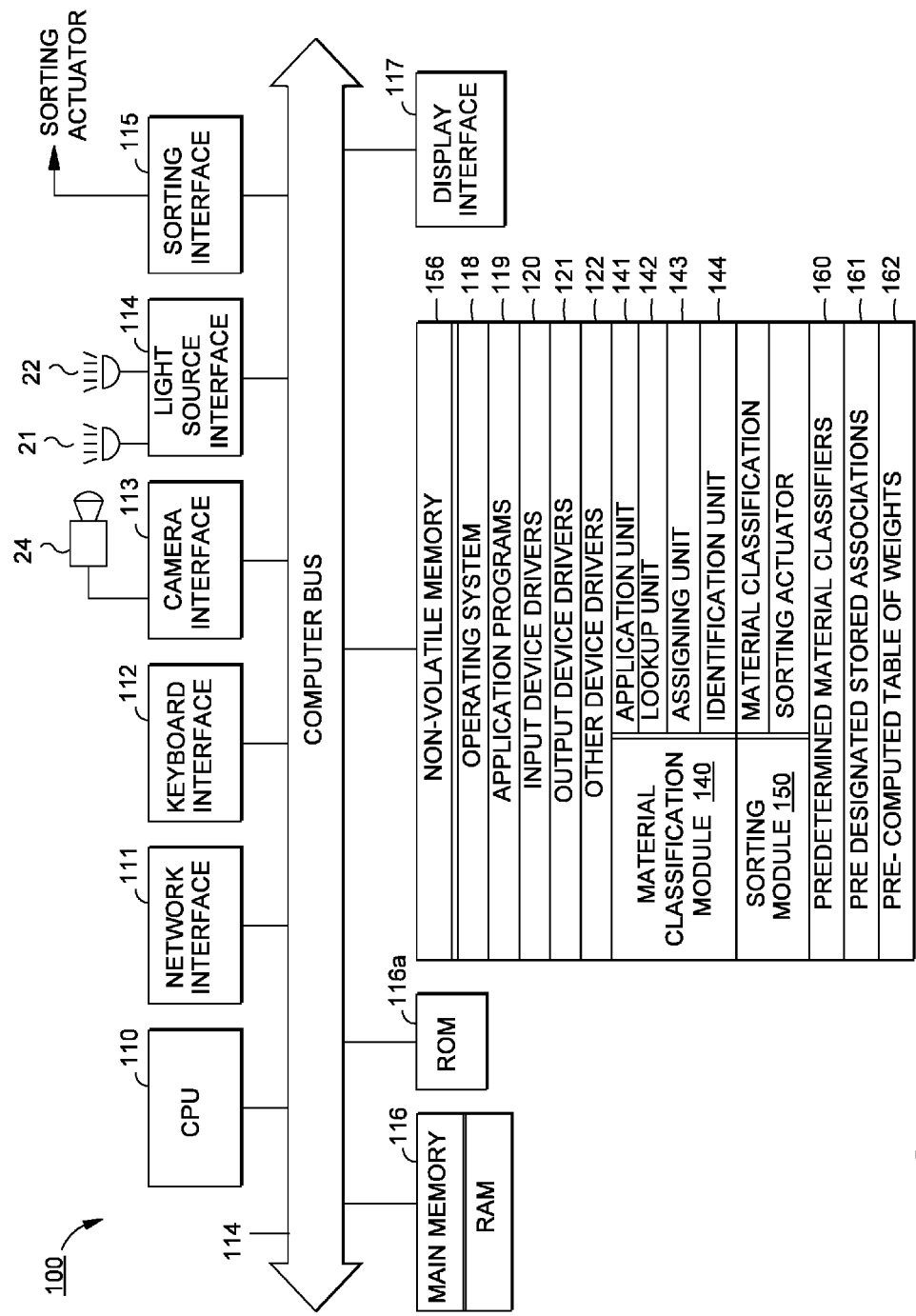
FIG. 2 is a view for explaining the architecture of a classification and sorting controller.

FIG. 2 is a view for explaining the architecture of classification and sorting controller 100.

As shown in FIG. 2, classification and sorting controller 100 includes central processing unit (CPU) 110 which interfaces with computer bus 114. Also interfacing with computer bus 114 are non-volatile memory 156 (e.g., a hard disk or other nonvolatile storage medium), network interface 111, keyboard interface 112, camera interface 113, random access memory (RAM) 116 for use as a main run-time transient memory, read only memory (ROM) 116a, and display interface 117 for a display screen or other output.

RAM 116 interfaces with computer bus 114 so as to provide information stored in RAM 116 to CPU 110 during execution of the instructions in software programs, such as an operating system, application programs, image processing modules, and device drivers. More specifically, CPU 110 first loads computer-executable process steps from non-volatile memory 156, or another storage device into a region of RAM 116. CPU 110 can then execute the stored process steps from RAM 116 in order to execute the loaded computer-executable process steps. Data, also, can be stored in RAM 116 so that the data can be accessed by CPU 110 during the execution of the computer-executable software programs, to the extent that such software programs have a need to access and/or modify the data.

As also shown in FIG. 2, non-volatile memory 156 contains computer-executable process steps for operating system 118, and application programs 119, such as graphic image management programs. Non-volatile memory 156 also contains computer-executable process steps for device drivers for software interface to devices, such as input device drivers 120, output device drivers 121, and other device drivers 122. In addition, a collection of plural predetermined material classifiers 160, predesignated stored associations 161 and pre-computed table of weights 162 is stored in non-volatile memory 156.

Non-volatile memory 156 also stores a material classification module 140 and a sorting module 150. The material classification module 140 and the sorting module 150 comprise computer-executable process steps for material classification of an object fabricated from an unknown material, and for sorting the object based on the material classification. As shown in FIG. 2, material classification module 140 generally comprises application unit 141, lookup unit 142, assigning unit 143 and identification unit 144. In some example embodiments, the material classification module also includes a corresponding plurality of modules for control of the light sources, for control of the camera(s) and for gathering of image data of such camera(s), a module for derivation of feature vectors according to a feature vector algorithm, such as feature vectors based on texture discrimination, spectral signature, BRDF, and a bidirectional surface scattering reflectance distribution function, and a classification machine. The classification machine accepts as inputs the feature vectors derived by the feature vector module, and provides a classification of the material from which the object under inspection is fabricated.

Sorting module 150 for its part includes a corresponding plurality of modules related to input of material classification from the classification machine, and actuation of the sorting mechanism based on the classification.

The computer-executable process steps for these modules may be configured as part of operating system 118, as part of an output device driver in output device drivers 121, or as a stand-alone application program. These modules may also be configured as a plug-in or dynamic link library (DLL) to the operating system, device driver or application program. It can be appreciated that the present disclosure is not limited to these embodiments and that the disclosed modules may be used in other environments.

Figure 3:
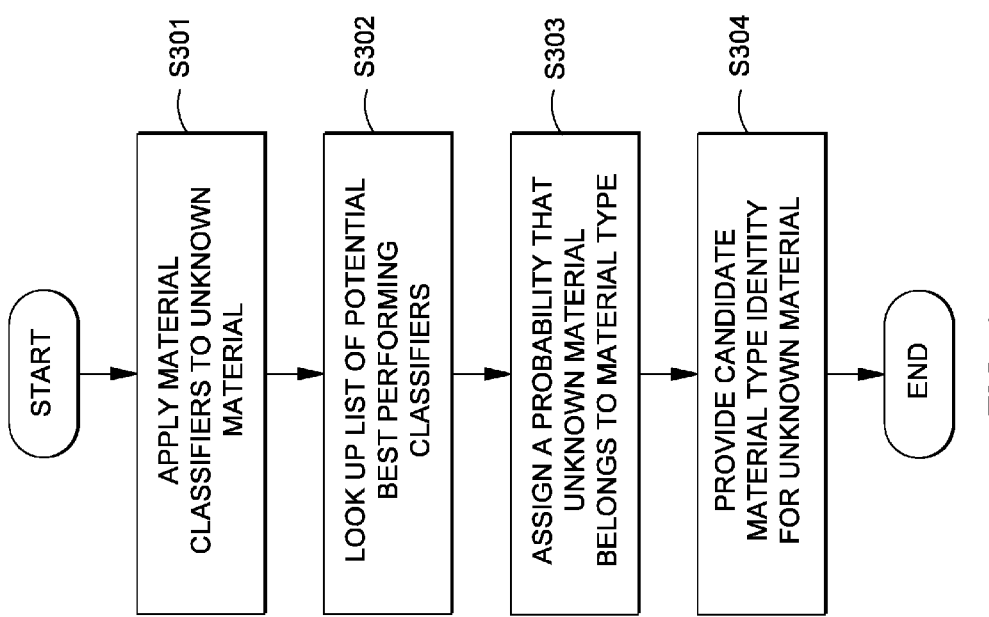
FIG. 3 is a flow diagram for explaining a process for classifying a material according to example embodiments.

FIG. 3 is a flow diagram for explaining a process for classifying a material according to an example embodiment. Briefly, in FIG. 3, an unknown material is classified into a probability distribution of multiple predetermined material types by using a collection of plural predetermined material classifiers 160.

With respect to the multiple predetermined material types, the multiple predetermined material types can include plastic, metal, fabric and glass, among other things. The material types can also include a fabric type such as cotton or polyester, and a plastic type such as PET (polyethylene terephthalate) or HIPS (high impact polystyrene). Each material type of the multiple predetermined material types is associated with a corresponding best performing classifier from the collection of plural predetermined material classifiers 160 by a predesignated stored association 161.

The collection of predetermined material classifiers 160 includes a classifier based on texture discrimination, a classifier based on a spectral signature, a classifier based on a bidirectional reflectance distribution function and a classifier based on a bidirectional surface scattering reflectance distribution function. Of course, all of these material classifiers do not have to be included in the collection, and other material classifiers can be included in the collection, such that the collection of material classifiers can be dynamically modified.

In more detail, in step S301, the plural predetermined material classifiers 160 are applied to the unknown material to obtain a list of candidate material types. In some example embodiments, applying the material classifiers 160 to the unknown material comprises obtaining one or more feature vectors for the unknown material and inputting a corresponding one of the feature vectors into each of the plural material classifiers. For example, the corresponding feature vector for a classifier based on texture discrimination is representative of texture of the unknown material. The corresponding feature vector for a classifier based on a spectral signature is representative of spectral reflectance of the unknown material. The corresponding feature vector for a classifier based on a bidirectional reflectance distribution function is representative of an angular dependence of reflectance of the unknown material. The corresponding feature vector for a classifier based on a bidirectional surface scattering reflectance distribution function is representative of a subsurface scattering property of the unknown material.

As a result of applying the plural material classifiers 160 to the unknown material, an output representative of material type from each of the plural material classifiers is obtained. The list of candidate material types includes the outputs from each of the plural material classifiers.

In some example embodiments, the output of each material classifier is indicative of a probability that the unknown material belongs to each material type. A candidate material type from such output corresponds to the material type with a highest probability. In other example embodiments, the output of each material classifier identifies a candidate material type that the unknown material belongs to.

In step S302, a list of potential best performing classifiers is looked up using the list of candidate material types as a reference into the predesignated stored association 161. In some example embodiments, the predesignated stored association 161 by which each material type is associated with a corresponding best performing classifier is based on empirical data from precise test data or labeled test samples. In other example embodiments, the predesignated stored association by which each material type is associated with a corresponding best performing classifier is based on theoretical behavior of the classifiers on the material types, without relying on empirical data or training data. For example, if it is known that a classifier is favorably accurate for materials having distinctive textures, the predesignated association is stored to associate textured materials, such as wood or fabric, with that classifier. As another example, the predesignated stored association can be based on the assumption that a spectral classifier is more accurate for material types with a distinctive spectral signature, such that a roughened metal like copper is associated with the spectral classifier. As a further example, if a classifier is favorably accurate for materials where the appearance of the material depends on the angle of viewing (e.g., a classifier based on a BRDF), the predesignated association is stored to associate polished metals with that classifier.

According to some example embodiments, the predesignated stored association 161 by which each material type is associated with a corresponding best performing classifier is stored in a look up table. Of course, the predesignated stored association can also be stored based on a combination of these approaches.

In step S303, a respective probability that the unknown material belongs to a material type is assigned based on the list of potential best performing classifiers. This assignment is performed by determining a weight for each of the plural predetermined material classifiers using the list of potential best performing classifiers, and assigning a respective probability that the unknown material belongs to a material type based on the weights of the plural predetermined material classifiers. In some example embodiments, assigning a respective probability that the unknown material belongs to a material type based on the weights of the plural predetermined material classifiers is accomplished by calculating a weighted combination of the plural predetermined material classifiers using the weights.

According to some embodiments, determining a weight for each of the plural predetermined material classifiers comprises a look up from a pre-computed table of weights 162. According to other example embodiments, determining a weight for each of the plural predetermined material classifiers comprises using a state machine that describes the behavior of the plural predetermined material classifiers, and finding a limit cycle of the state machine. This process will be discussed in more detail below.

In step S304, a candidate material type identity is provided for the unknown material based on the assigned probabilities of the material types. Of course, in other example embodiments, step S304 can be omitted if a definite answer of material type is not required.

Combining Two Material Classifiers

A case will now be considered where two predetermined material classifiers are included in the collection. In this example, classifier $T_A$ is based on a texture approach and classifier $T_B$ is based on a spectral approach. In order to determine a material type for an unknown material w, classifier $T_A$ returns an index $i \in \{1, 2, \ldots, n\}$, i.e., unknown material w is identified as material type i, where n is the number of material types.

If $T_A(w)$ is assumed to be a probability distribution, the special case that a single material type i is identified then corresponds to:

$$T_A(w) = \delta(x-i), \delta(x) = \begin{cases} 1 & \text{if } x = 0 \\ 0 & \text{if } x \neq 0 \end{cases} \quad \text{(Equation 1)}$$

In this example, the number of material types is 8 (n=8) as shown in the following Table 1. Of course, the number of material types can be any reasonable number. According to some embodiments, a numerical count of the multiple predetermined material types is countably small based on the processing capabilities of the classification controller. In some example embodiments, a number of the multiple predetermined material types is anywhere from 2 to 100, and is often larger than the number of predetermined material classifiers.

TABLE 1

|  | M1 | M2 | M3 | M4 | M5 | M6 | M7 | M8 |
|---|---|---|---|---|---|---|---|---|
| $T_A$ | 82.00% | 73.30% | 98.40% | 90.30% | 93.40% | 72.70% | 88.50% | 98.40% |
| $T_B$ | 93.40% | 86.10% | 89.90% | 85.90% | 89.20% | 81.50% | 83.50% | 86.80% |

The performance of classifiers $T_A$ and $T_B$ relative to each material type M1 to M8 is indicated by a recognition rate. In this example, the recognition rate is determined empirically by applying classifiers $T_A$ and $T_B$ to a set of labeled test samples.

Of course, other approaches for determining the recognition rate can be used, as previously discussed. As one example, the predesignated stored association by which each material type is associated with a corresponding best performing classifier can be based on an assumption regarding the theoretical behavior of the classifiers on the material types, without relying on empirical data or training data. For example, if it is known that a classifier is favorably accurate for materials having distinctive textures, the predesignated association is stored to associate textured materials, such as wood or fabric, with that classifier. As another example, the predesignated stored association can be based on the assumption that a spectral classifier is more accurate for material types with a distinctive spectral signature, such that a roughened metal like copper is associated with the spectral classifier. As a further example, if a classifier is favorably accurate for materials where the appearance of the material depends on the angle of viewing (e.g., a classifier based on a BRDF), the predesignated association is stored to associate polished metals with that classifier.

As shown in Table 1, classifier $T_A$ performs more accurately for material types M3, M4, M5, M7 and M8, while classifier $T_B$ performs more accurately for material types M1, M2 and M6.

One possible approach to combining classifiers $T_A$ and $T_B$ is to simply average the output probability distribution of each classifier. Using this approach, a new classifier $S_0$ is constructed such that for an unknown material w, $$S_0(w)=0.5T_A(w)+0.5T_B(w) \quad \text{(Equation 2)}$$

An example result of applying Equation (2) to material types M1 to M8 is shown below in Table 2.

TABLE 2

|  | M1 | M2 | M3 | M4 | M5 | M6 | M7 | M8 |
|---|---|---|---|---|---|---|---|---|
| $T_A$ | 82.00% | 73.30% | 98.40% | 90.30% | 93.40% | 72.70% | 88.50% | 98.40% |
| $T_B$ | 93.40% | 86.10% | 89.90% | 85.90% | 89.20% | 81.50% | 83.50% | 86.80% |
| $S_0$ | 87.70% | 79.70% | 94.15% | 88.10% | 91.30% | 77.10% | 86.00% | 92.60% |

If each material type M1 to M8 is associated with the corresponding material classifier that performs most accurately for the particular material type (e.g., M1 is associated with "B" because $T_B$ is the classifier that performs most accurately for it and M3 is associated with "A" because $T_A$ is the classifier that performs most accurately for it), the following look up Table 3 is generated based on the example in Table 1:

TABLE 3

|  | M1 | M2 | M3 | M4 | M5 | M6 | M7 | M8 |
|---|---|---|---|---|---|---|---|---|
| Best Perf. Classifier | B | B | A | A | A | B | A | A |

Table 3 stores a predesignated stored association, by which each material type M1 to M8 is associated with a corresponding best performing classifier $T_A$ or $T_B$. Analyzing the example in Table 3, the weights [0.5, 0.5] in Equation (2), which represents a weight distribution for classifiers $T_A$ and $T_B$, are seen to be suboptimal. Based on the predesignated associations in Table 3, the optimal weights are $[\alpha, 1-\alpha]$, where $\alpha$ depends on cl(w), the best performing classifier of the unknown material w. A combined classifier is constructed as follows:

$$S_{optimal}(w)=\alpha(cl(w))T_A(w)+(1-\alpha(cl(w)))T_B(w) \quad \text{(Equation 3)}$$

To implement Equation (3) directly, knowledge of cl(w), which is the association between unknown materials and best performing classifiers, is required. However, cl(w) is not known because the predesignated stored association in Table 3 associates material types with best performing classifiers, not unknown materials with best performing classifiers. In order to implement Equation (3) to combine classifiers $T_A$ and $T_B$, cl(w) is approximated by cl($T_A$(w)) and cl($T_B$(w)). More specifically, if $T_A$(w) or $T_B$(w) is a delta probability distribution, then cl($T_A$(w)) or cl($T_B$(w)) is obtained by using a look up table such as Table 3. If $T_A$(w) or $T_B$(w) is a general probability distribution, then the material type with highest probability is determined and then the material type is used to perform a look up from a table such as Table 3.

Figure 4:
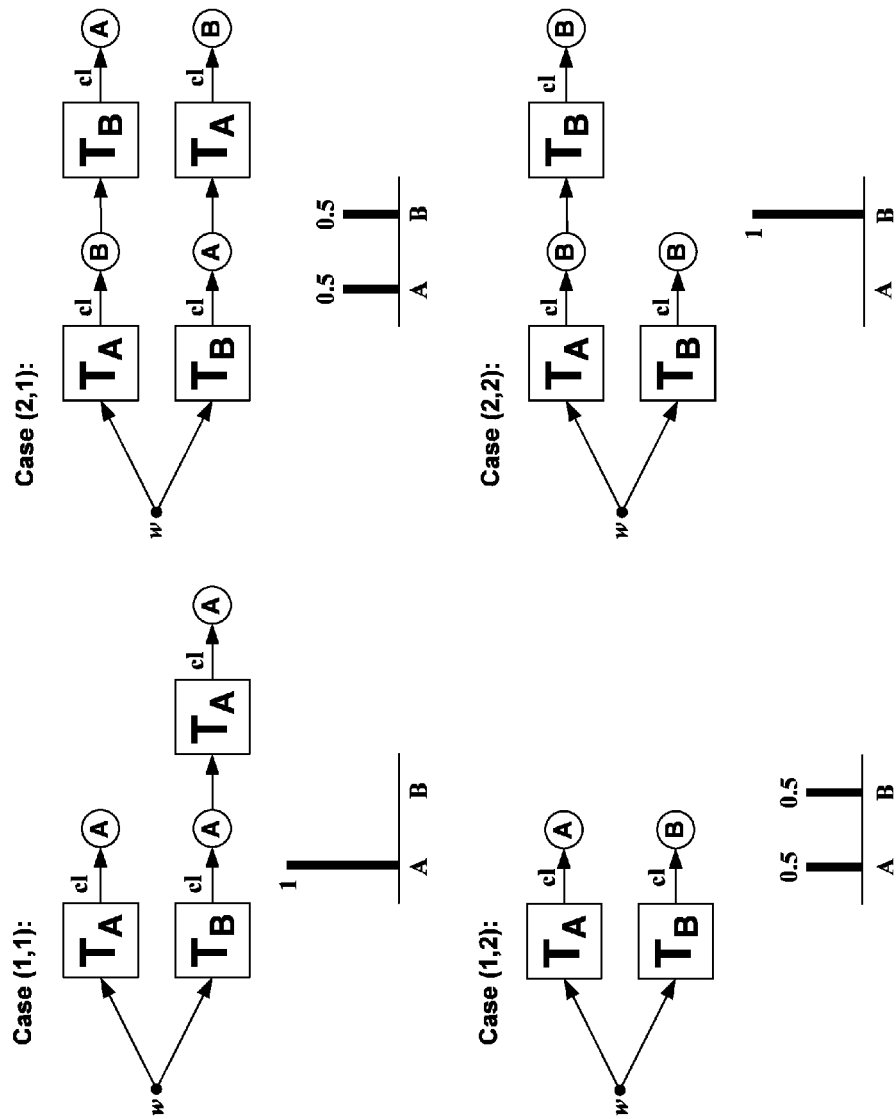
FIG. 4 is a view for explaining a process for combining two classifiers according to an example embodiment.

Because cl($T_A$(w))$\in$\{A, B\} and cl($T_B$(w))$\in$\{A, B\}, there are generally four cases, which are illustrated in FIG. 4, where the weight distribution for the classifiers, $[\alpha, 1-\alpha]$, is also shown.

Considering the general case where the number of material classifiers in the collection is m (i.e., $T_1, T_2, \ldots, T_m$) then a list of candidate material types [$T_1$(w), $T_2$(w), $T_m$(w)] is determined. Using the list of candidate material types, a list of potential best performing classifiers [$I_1, I_2, \ldots, I_m$] is determined as follows:

$$[I_1, I_2, \ldots, I_m]=[cl(T_1(w)), cl(T_2(w)), \ldots, cl(T_m(w))] \quad \text{(Equation 4)}$$

In this example, the operation "cl" is implemented as a predetermined look up table similar to the example of Table 3, but with m possible output values 1, 2, . . . , m.

A weight distribution of the classifiers, $w^{(1)}(x)$, is calculated using the following Equation (5):

$$w^{(1)}(x) = \frac{1}{m}\sum_{i=1}^{m}\delta(x-I_i) \quad \text{(Equation 5)}$$

The superscript "(1)" refers to "one iteration" and its meaning will be apparent when limit cycles of a state machine are discussed in detail below. If Equation (5) is applied to the cases shown in FIG. 4, the results are as follows:

For case (1, 1), where $cl(T_A(w))=cl(T_B(w))=$"A" which is also identified with label "1" (and similarly "B" identified with label "2"), the weight distribution is:

$$w^{(1)}(x) = \frac{1}{2}(\delta(x-1) + \delta(x-1)) = \delta(x-1).$$

This can also be written as a list of weights: $w^{(1)}=[w_1^{(1)}, w_2^{(1)}]=[1,0]$ For case (2, 1), the weight distribution is $$w^{(1)}(x) = \frac{1}{2}(\delta(x-2) + \delta(x-1)) = 0.5\delta(x-1) + 0.5\delta(x-2).$$

This can also be written as a list of weights: $w^{(1)}=[w_1^{(1)}, w_2^{(1)}]=[0.5,0.5]$ For case (1, 2), the weight distribution is $$w^{(1)}(x) = \frac{1}{2}(\delta(x-2) + \delta(x-1)) = 0.5\delta(x-1) + 0.5\delta(x-2).$$

This can also be written as a list of weights: $w^{(1)}=[w_1^{(1)}, w_2^{(1)}]=[0.5,0.5]$ Finally, for case (2, 2), the weight distribution is $$w^{(1)}(x) = \frac{1}{2}(\delta(x-2) + \delta(x-2)) = \delta(x-2).$$

This can also be written as a list of weights: $w^{(1)}=[w_1^{(1)}, w_2^{(1)}]=[0,1]$ A probability distribution for the unknown material w is assigned, indicating a particular material type for the unknown material w. The resulting combined classifier $S_1$ is represented by Equation (6) as follows:

$$S_1(w) = \sum_{x=1}^{m} w^{(1)}(x) T_x(w) \qquad \text{(Equation 6)}$$

The result of applying Equation (6) to the example discussed above in Table 2 is shown below in Table 4:

As can be seen from Table 4, $S_1$ exceeds performance of both original classifiers $T_A$ and $T_B$ for some material types. This advantage is due at least in part to the effect of combining classifiers $T_A$ and $T_B$ to construct $S_1$, since there might be materials that are misclassified by only one of classifiers $T_A$ and $T_B$, such that combining $T_A$ and $T_B$ to construct $S_1$ allows correct classification at a higher rate.

Combining Three or More Material Classifiers

Before moving to the case where three or more predetermined material classifiers are included in the collection (i.e., m>2), the example of FIG. 4 discussed above will first be discussed with respect to finite state machines.

Figure 5:
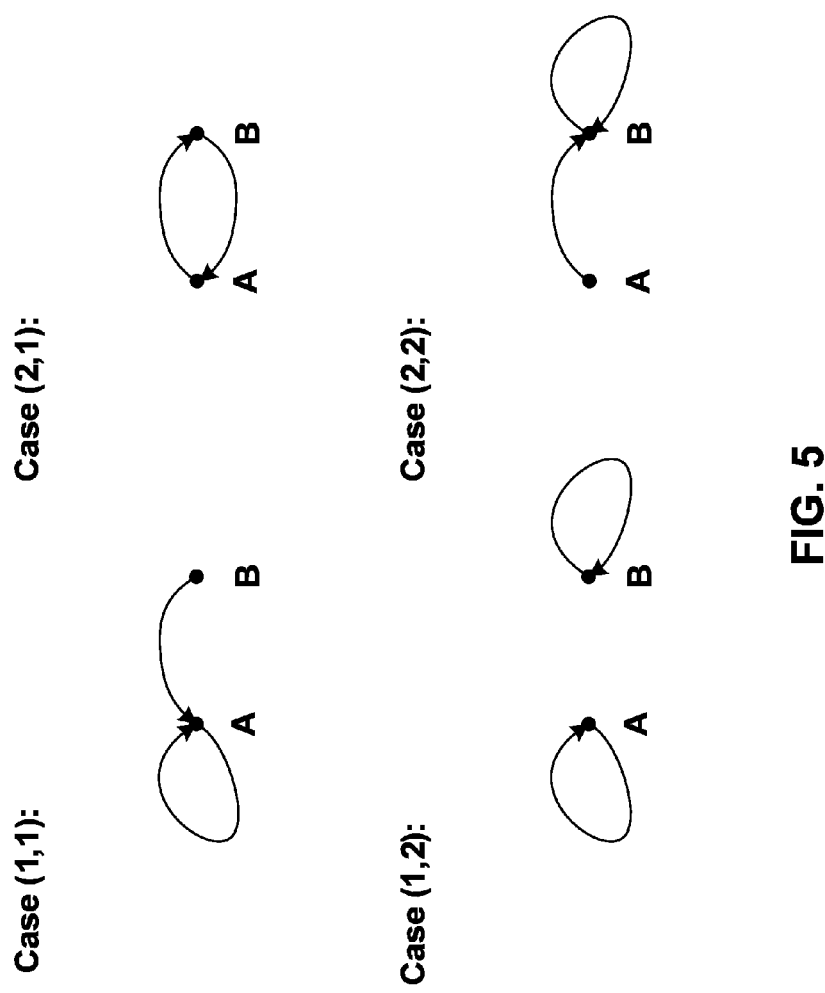
FIG. 5 is a view for explaining a state machine according to an example embodiment in which the number of material classifiers is two.

In more detail, FIG. 5 is a view representing state diagrams used in finite state machines (e.g., automata). As shown in FIG. 5, each classifier $T_A$ and $T_B$ is represented as a state "A" or "B". A transition (indicated by a directed edge) from state i to state j exists if $cl(T_i(w))=j$. A limit cycle of the state machine is determined, by performing repeated iterations using the state machine. A limit cycle consists of l states ($i_1, i_2, \ldots, i_l$). If l=1, it is determined that there is a fixed point.

The state diagrams shown in FIG. 5 are based on the example cases of FIG. 4. Using the example of FIG. 4, in case (1, 1), state "A" enters into a limit cycle of length 1, (A), and state "B" also enters into a limit cycle of length 1, (A). In case (2, 1), both states "A" and "B" enter into a limit cycle of length 2, (A, B). In case (1, 2), state "A" enters into a limit cycle of length 1, (A) while state "B" enters into a different limit cycle of length 1, (B). Finally, in case (2, 2), both states "A" and "B" enter into a limit cycle of length 1, (B).

According example embodiments, the notion of limit cycle is used to determine the weight distribution of the classifiers, as discussed in more detail below. This is particularly useful in situations where the number of material classifiers is greater than two.

In order to facilitate explanation of the case where three or more predetermined material classifiers are included in the collection, the example of Table 1 will be expanded to include a classifier $T_C$. In this example, the recognition rate for classifier $T_C$ is determined in the same manner as for classifiers $T_A$ and $T_B$. Accordingly, the rate is determined empirically by applying classifier $T_C$ to a set of labeled test samples.

Of course, the predesignated stored association can also be determined using a theoretical assumption about the behavior of the classifiers.

According to this example, the best performing classifiers for the material types M1 to M8 have 3 possible values, "A", "B" or "C", as shown in Table 5 below:

TABLE 4

|  | M1 | M2 | M3 | M4 | M5 | M6 | M7 | M8 |
|---|---|---|---|---|---|---|---|---|
| $T_A$ | 82.00% | 73.30% | 98.40% | 90.30% | 93.40% | 72.70% | 88.50% | 98.40% |
| $T_B$ | 93.40% | 86.10% | 89.90% | 85.90% | 89.20% | 81.50% | 83.50% | 86.80% |
| $S_0$ | 87.70% | 79.70% | 94.15% | 88.10% | 91.30% | 77.10% | 86.00% | 92.60% |
| $S_1$ | 87.65% | 89.10% | 94.15% | 87.75% | 92.50% | 84.00% | 88.40% | 98.55% |

TABLE 5

|   | M1 | M2 | M3 | M4 | M5 | M6 | M7 | M8 |
|---|---|---|---|---|---|---|---|---|
| $T_A$ | 82.00% | 73.30% | 98.40% | 90.30% | 93.40% | 72.70% | 88.50% | 98.40% |
| $T_B$ | 93.40% | 86.10% | 89.90% | 85.90% | 89.20% | 81.50% | 83.50% | 86.80% |
| $T_C$ | 76.50% | 99.60% | 83.80% | 77.30% | 76.30% | 72.50% | 97.70% | 85.00% |
| Best Perf. Classifier | B | C | A | A | A | B | C | A |

Table 5 is a look up table storing a predesignated stored association, by which each material type M1 to M8 is associated with a corresponding best performing classifier $T_A$, $T_B$ or $T_C$.

Figure 6:
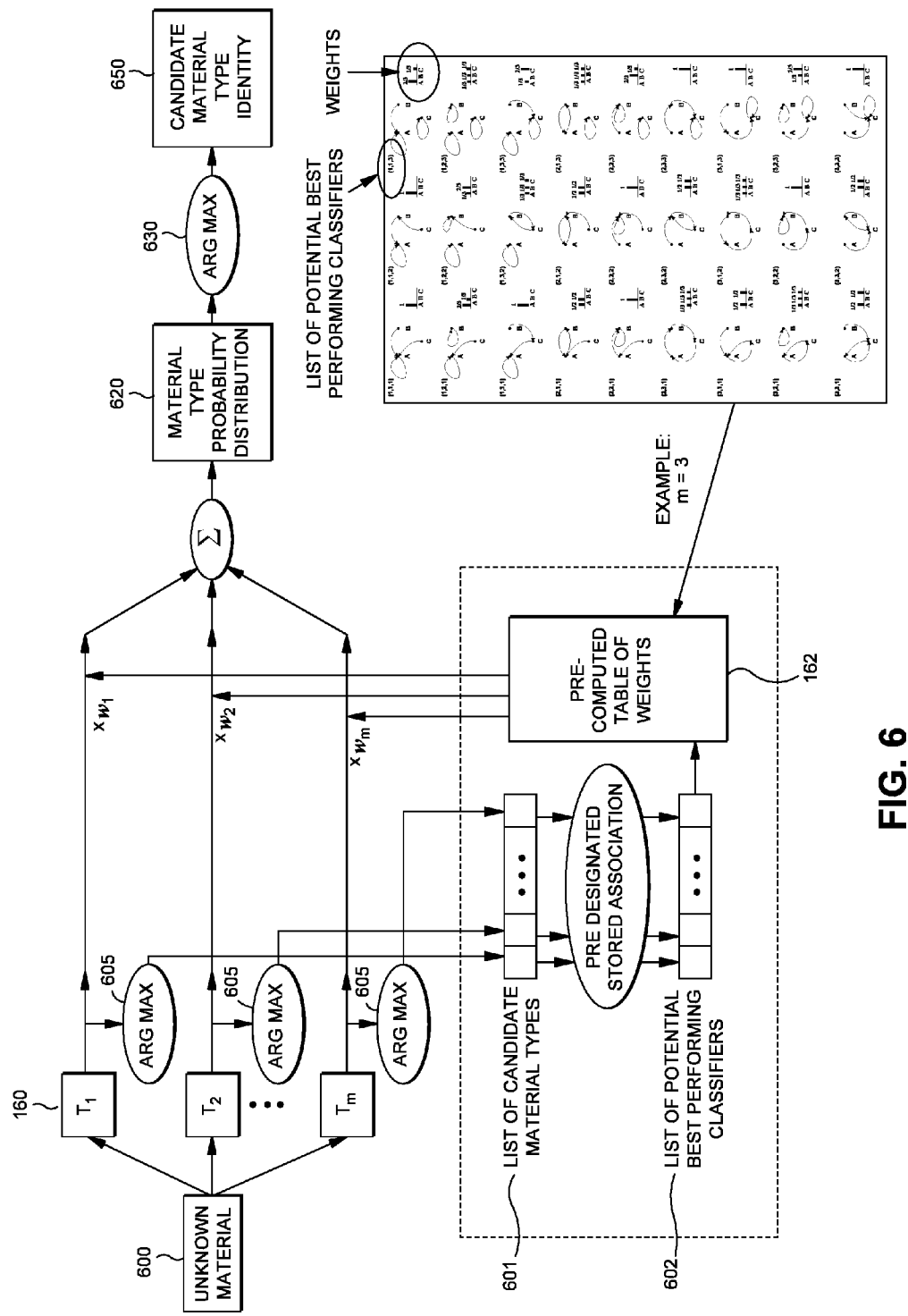
FIG. 6 is a representative view for explaining a process for classifying a material according to an example embodiment.

FIG. 6 is a representative view for explaining a process for classifying a material according to an example embodiment in which the number of predetermined material classifiers 160 is three (i.e., m=3).

Considering the general case where there are m classifiers $T_1, T_2, \ldots, T_m$, for an unknown material w (600), a list of candidate material types 601 is determined. The list of candidate material types 601 is represented by: $[T_1(w), T_2(w), \ldots, T_m(w)]$, and is determined by applying each of classifiers 160 in order to obtain a probability distribution representing the likelihood that the unknown material is of a particular material type. As shown in FIG. 6, the most probable material type output from each material classifier is determined by obtaining the "argument at maximum value" 605 of each probability distribution. According to this example, the argument at maximum value 605 of each probability distribution returns the material type that has the highest probability from among the multiple predetermined material types, and outputs this material type to generate the list of candidate material types 601. The list of candidate material types 601 comprises the collection of these outputs from the classifiers $T_1, T_2, \ldots, T_m$.

Turning to the process of determining how to combine classifiers 160, the list of candidate material types 601 is used to determine a list of potential best performing classifiers 602, represented by $[I_1, I_2, \ldots, I_m]$, as follows:

$$[I_1, I_2, \ldots, I_m] = [cl(T_1(w)), cl(T_2(w)), \ldots, cl(Tm(w))] \quad \text{(Equation 7)}$$

More specifically, the list of candidate material types 601 is used as a key to reference the predesignated stored associations 161, in order to generate a list of potential best performing classifiers 602. In this regard, based on the list of candidate material types 601 and the predesignated stored associations 161, a list of potential best performing classifiers 602 is determined. In this example, the predesignated stored association $cl(T_m(w))$ is implemented as a predetermined look up table similar to the example in the last row of Table 5, but with m possible output values 1, 2, ..., m.

The list of potential best performing classifiers 602 is input to a pre-computed table of weights 162, and the weights that are used to combine classifiers $T_1, T_2, \ldots, T_m$ are output.

Figure 7:
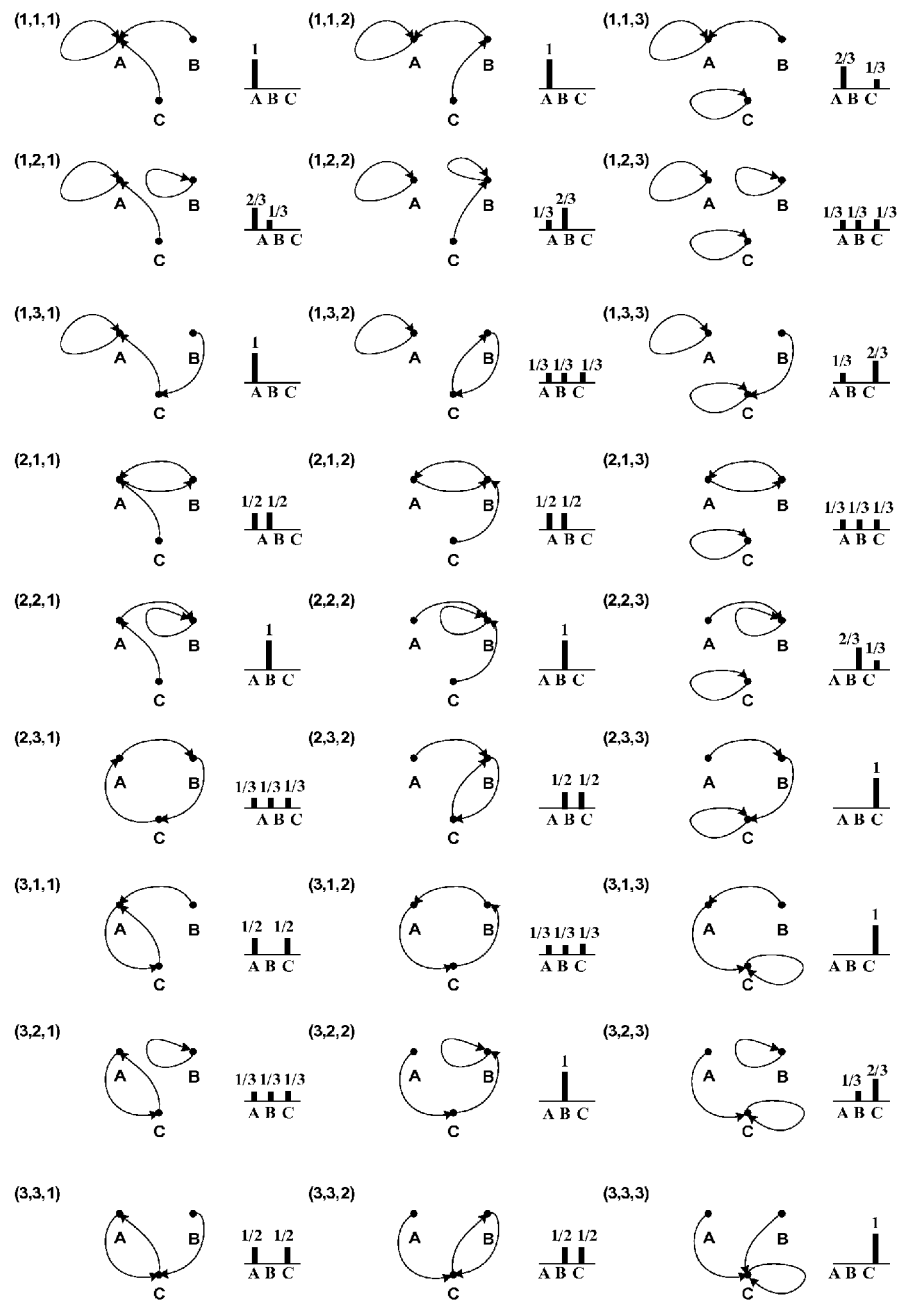
FIG. 7 is a view for explaining a state machine according to an example embodiment in which the number of material classifiers is three.

With respect to pre-computing the table of weights, for the case where the number of material classifiers m=3, it is determined that there are $3^3=27$ state diagrams, which are represented in FIG. 6 and in more detail in FIG. 7. FIGS. 6 and 7 also show weight distributions for the material classifiers, which are based on the limit cycles. The state diagrams shown in FIGS. 6 and 7 are used to pre-compute the weights that are used to combine classifiers $T_1, T_2, \ldots, T_m$ to populate the pre-computed table of weights. In particular, the list of potential best performing classifiers 602 calculated using Equation (7) is used to label the 27 cases in FIG. 7. In addition, list 602 determines the transitions in the finite state machine that describe the behavior of the classifiers included in the list 602. More specifically, a transition exists and only exists from state i to state L. A dynamical system on m states is associated with the finite state machine. For each initial state $I \in \{1, 2, \ldots, m\}$, the limit cycle is determined using the process shown in FIG. 8, discussed below.

If the limit cycle for state I is represented as $(J_{1,I}, J_{2,I}, \ldots, J_{l(I),I})$, where the length of the limit cycle l(I) depends on I, a weight distribution for the classifiers is determined as shown in Equation (8):

$$w^{(\infty)}(x) = \frac{1}{m}\sum_{I=1}^{m}\frac{1}{l(I)}\sum_{i=1}^{l(I)}\delta(x - J_{i,I}) \quad \text{(Equation 8)}$$

Equation (8) yields a different weight distribution than Equation (5) discussed above. To illustrate this, consider case (2, 1, 2) as shown in FIG. 7. Applying Equation (5) to case (2, 1, 2) results in the following weight distribution:

$$w^{(1)}(x) = \frac{1}{3}(\delta(x-2) + \delta(x-1) + \delta(x-2)) = \frac{1}{3}\delta(x-1) + \frac{2}{3}\delta(x-2).$$

This can be written as a list of weights:

$$w^{(1)} = [w_1^{(1)}, w_2^{(1)}, w_3^{(1)}] = \left[\frac{1}{3}, \frac{2}{3}, 0\right]$$

To apply Equation (8), the limit cycle is calculated for each state as follows:
State 1 ("A"): (1, 2)
State 2 ("B"): (1, 2)
State 3 ("C"): (1, 2)
Using this state information, the weight distribution according to Equation (8) is determined as follows:

$$w^{(\infty)}(x) = \frac{1}{3}\left\{\begin{array}{c}\frac{1}{2}[\delta(x-1) + \delta(x-2)] + \frac{1}{2}[\delta(x-1) + \delta(x-2)] + \\ \frac{1}{2}[\delta(x-1) + \delta(x-2)]\end{array}\right\}$$

$$= \frac{1}{2}\delta(x-1) + \frac{1}{2}\delta(x-2)$$

This can be written as a list of weights:

$$w^{(\infty)} = [w_1, w_2, w_3] = \left[\frac{1}{2}, \frac{1}{2}, 0\right]$$

A probability distribution 620 for the unknown material w is then assigned, indicating the probability that the unknown material belongs to a particular material type. The output of the combined classifier $S_\infty$ is determined as follows:

$$S_\infty(w) = \sum_{x=1}^{m} w^{(\infty)}(x)T_x(w) = \sum_{x=1}^{m} w_x T_x(w) \qquad \text{(Equation 9)}$$

According to some embodiments, a candidate material type identity 650 is then provided for the unknown material w based on the assigned probability distribution. For example, the identity of the unknown material can be provided by obtaining the argument at maximum value 630 of the probability distribution. According to this example, the argument at maximum value 630 of the probability distribution returns the material type which has the highest probability from among the multiple predetermined material types, and outputs this material type as the candidate material type identity.

An example result is shown below in Table 6, where all the combined material classifiers proposed in this disclosure are compared for the case m=3. Note that $S_o$ is defined in this example by $$S_0(w) = \frac{1}{3}T_A(w) + \frac{1}{3}T_B(w) + \frac{1}{3}T_C(w).$$

TABLE 6

|  | M1 | M2 | M3 | M4 | M5 | M6 | M7 | M8 |
|---|---|---|---|---|---|---|---|---|
| $T_A$ | 82.00% | 73.30% | 98.40% | 90.30% | 93.40% | 72.70% | 88.50% | 98.40% |
| $T_B$ | 93.40% | 86.10% | 89.90% | 85.90% | 89.20% | 81.50% | 83.50% | 86.80% |
| $T_C$ | 76.50% | 99.60% | 83.80% | 77.30% | 76.30% | 72.50% | 97.70% | 85.00% |
| $S_0$ | 83.97% | 86.33% | 90.70% | 84.50% | 86.30% | 75.57% | 89.90% | 90.07% |
| $S_1$ | 87.93% | 96.13% | 91.20% | 87.17% | 91.73% | 82.53% | 93.73% | 98.07% |
| $S_\infty$ | 88.60% | 96.20% | 91.40% | 87.82% | 91.83% | 84.70% | 93.93% | 98.20% |

As can be seen from results shown in Table 6, $S_\infty$ has the best performance across all material types M1 to M8.

Of course, although the example discussed above is a case where the number of material classifiers is three, the number of predetermined material classifiers can be any reasonable number based on the processing capabilities of the classification controller. In some example embodiments, the number of predetermined material classifiers can be anywhere from 2 to 5, and often will be smaller than the number of material types.

In some example embodiments, Equation (5) and Equation (8) can be implemented as look up tables that are pre-computed and stored. In this case, for a given list of potential best performing classifiers, each weight distribution is an array of m values. Since these m values add up to 1, if saving storage space is a priority for the classification system, only m−1 values need to be stored. There are $m^m$ possible lists of potential best performing classifiers, so that $m^m(m-1)$ values need to be pre-computed and stored. For small values of m, very little storage is needed to implement Equations (5) and (8). By way of example, in a case where m=2, 4 values need to be stored, and in a case where m=3, 54 values need to be stored.

Figure 8:
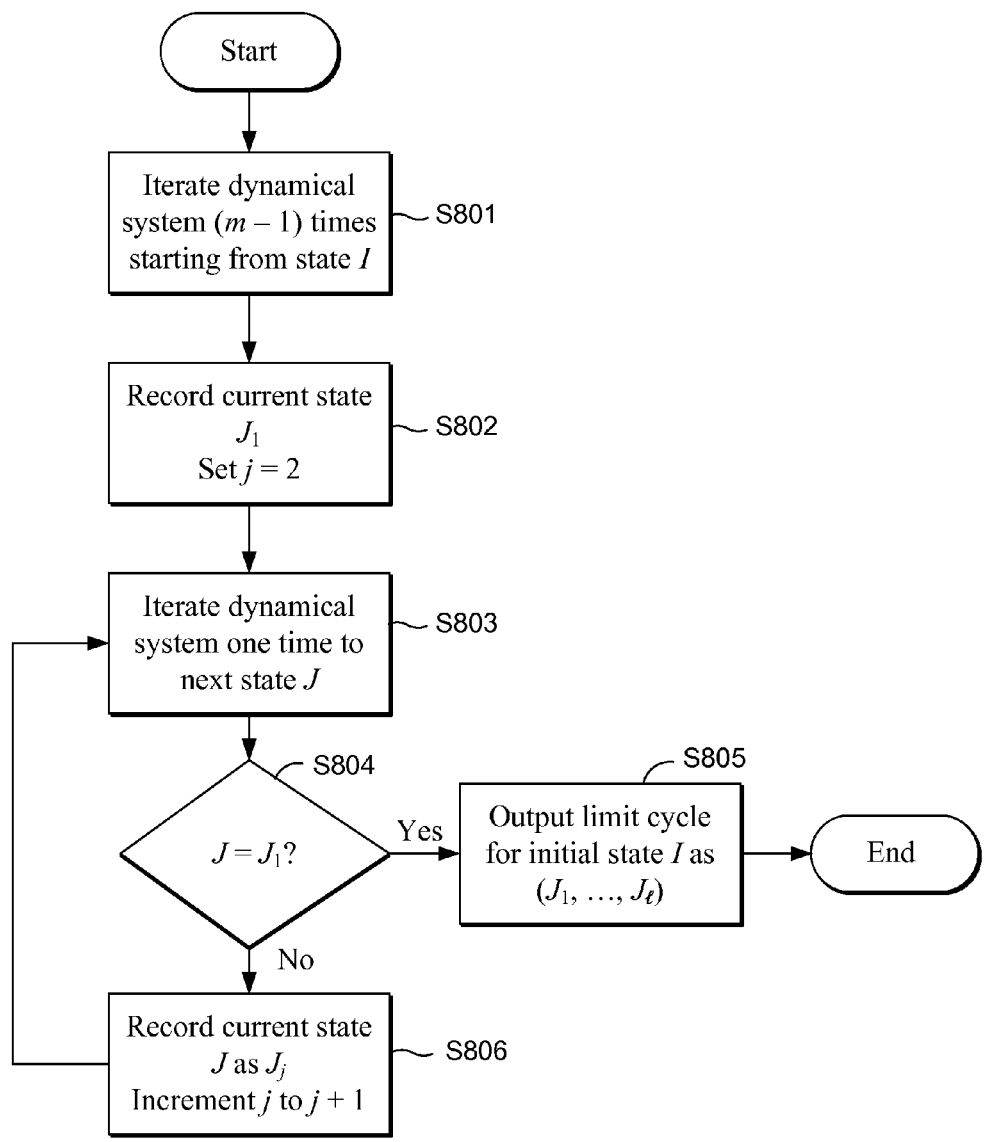
FIG. 8 is a view for explaining calculation of a limit cycle according to an example embodiment.

FIG. 8 is a view for explaining calculation of a limit cycle according to an example embodiment. As shown in FIG. 8, in step S801, the state machine performs (m−1) iterations of the system describing the behavior of the material classifiers, beginning from an initial state I. In step S802, the initial current state is recorded, and a count variable j is set to 2. In step S803, the state machine performs one iteration of the system to the next state. In step S804, it is determined whether the current state is the same as the previous state. If yes, in step S805, the limit cycle is output. If no, in step S806, the current state is recorded and the count variable j is increased by one.

Other Embodiments

According to other embodiments contemplated by the present disclosure, example embodiments may include a computer processor such as a single core or multi-core central processing unit (CPU) or micro-processing unit (MPU), which is constructed to realize the functionality described above. The computer processor might be incorporated in a stand-alone apparatus or in a multi-component apparatus, or might comprise multiple computer processors which are constructed to work together to realize such functionality. The computer processor or processors execute a computer-executable program (sometimes referred to as computer-executable instructions or computer-executable code) to perform some or all of the above-described functions. The computer-executable program may be pre-stored in the computer processor(s), or the computer processor(s) may be functionally connected for access to a non-transitory computer-readable storage medium on which the computer-executable program or program steps are stored. For these purposes, access to the non-transitory computer-readable storage medium may be a local access such as by access via a local memory bus structure, or may be a remote access such as by access via a wired or wireless network or Internet. The computer processor(s) may thereafter be operated to execute the computer-executable program or program steps to perform functions of the above-described embodiments.

According to still further embodiments contemplated by the present disclosure, example embodiments may include methods in which the functionality described above is performed by a computer processor such as a single core or multi-core central processing unit (CPU) or micro-processing unit (MPU). As explained above, the computer processor might be incorporated in a stand-alone apparatus or in a multi-component apparatus, or might comprise multiple computer processors which work together to perform such functionality. The computer processor or processors execute a computer-executable program (sometimes referred to as computer-executable instructions or computer-executable code) to perform some or all of the above-described functions. The computer-executable program may be pre-stored in the computer processor(s), or the computer processor(s) may be functionally connected for access to a non-transitory computer-readable storage medium on which the computer-executable program or program steps are stored. Access to the non-transitory computer-readable storage medium may form part of the method of the embodiment. For these purposes, access to the non-transitory computer-readable storage medium may be a local access such as by access via a local memory bus structure, or may be a remote access such as by access via a wired or wireless network or Internet. The computer processor(s) is/are thereafter operated to execute the computer-executable program or program steps to perform functions of the above-described embodiments.

The non-transitory computer-readable storage medium on which a computer-executable program or program steps are stored may be any of a wide variety of tangible storage devices which are constructed to retrievably store data, including, for example, any of a flexible disk (floppy disk), a hard disk, an optical disk, a magneto-optical disk, a compact disc (CD), a digital versatile disc (DVD), micro-drive, a read only memory (ROM), random access memory (RAM), erasable programmable read only memory (EPROM), electrically erasable programmable read only memory (EEPROM), dynamic random access memory (DRAM), video RAM (VRAM), a magnetic tape or card, optical card, nanosystem, molecular memory integrated circuit, redundant array of independent disks (RAID), a nonvolatile memory card, a flash memory device, a storage of distributed computing systems and the like. The storage medium may be a function expansion unit removably inserted in and/or remotely accessed by the apparatus or system for use with the computer processor(s).

This disclosure has provided a detailed description with respect to particular representative embodiments. It is understood that the scope of the appended claims is not limited to the above-described embodiments and that various changes and modifications may be made without departing from the scope of the claims.

What is claimed is:

1. A method of classifying the material type of an unknown material into a probability distribution of multiple predetermined material types by using a collection of plural predetermined material classifiers, wherein each material type of the multiple predetermined material types is associated with a corresponding best performing classifier from the collection of plural predetermined material classifiers by a predesignated stored association, the method comprising the steps of:
    applying, using a processor, the plural material classifiers to the unknown material to obtain a list of candidate material types;
    looking up, using the processor, a list of potential best performing classifiers using the list of candidate material types as a reference into the predesignated stored association; and
    assigning, using the processor, a respective probability that the unknown material belongs to a material type based on the list of potential best performing classifiers,
    wherein applying comprises obtaining one or more feature vectors for the unknown material and inputting a corresponding one of the feature vectors into each of the plural material classifiers so as to obtain an output representative of material type from each of the plural material classifiers.

2. The method according to claim 1, wherein the output of each material classifier is indicative of a probability that the unknown material belongs to each material type.

3. The method according to claim 1, wherein the output of each material classifier identifies a candidate material type that the unknown material belongs to.

4. The method according to claim 1, wherein the collection of plural material classifiers includes a classifier based on texture discrimination, and the corresponding feature vector for such classifier is representative of texture of the unknown material.

5. The method according to claim 1, wherein the collection of plural material classifiers includes a classifier based on a spectral signature, and the corresponding feature vector for such classifier is representative of spectral reflectance of the unknown material.

6. The method according to claim 1, wherein the collection of plural material classifiers includes a classifier based on a bidirectional reflectance distribution function, and the corresponding feature vector for such classifier is representative of an angular dependence of reflectance of the unknown material.

7. The method according to claim 1, wherein the collection of plural material classifiers includes a classifier based on a bidirectional surface scattering reflectance distribution function, and the corresponding feature vector for such classifier is representative of a subsurface scattering property of the unknown material.

8. The method according to claim 1, wherein assigning comprises:
    determining a weight for each of the plural predetermined material classifiers by using the list of potential best performing classifiers; and
    assigning a respective probability that the unknown material belongs to a material type based on the weights of the plural predetermined material classifiers.

9. The method according to claim 8, wherein determining a weight for each of the plural predetermined material classifiers comprises a look up from a pre-computed table of weights.

10. The method according to claim 8, wherein determining a weight for each of the plural predetermined material classifiers comprises using a state machine that describes the behavior of the plural predetermined material classifiers, and finding a limit cycle of the state machine.

11. The method according to claim 8, wherein assigning a respective probability that the unknown material belongs to a material type based on the weights of the plural predetermined material classifiers comprises calculating a weighted combination of the plural predetermined material classifiers using the weights.

12. The method according to claim 1, wherein the predesignated stored association by which each material type is associated with a corresponding best performing classifier is based on empirical data from labeled test samples.

13. The method according to claim 1, wherein the predesignated stored association by which each material type is associated with a corresponding best performing classifier is based on theoretical behavior of the classifiers on the material types.

14. The method according to claim 1, wherein the predesignated stored association by which each material type is associated with a corresponding best performing classifier is stored in a look up table.

15. The method according to claim 1, wherein the multiple predetermined material types includes a plastic type.

16. The method according to claim 1, wherein the multiple predetermined material types includes a metal type.

17. The method according to claim 1, wherein the multiple predetermined material types includes a fabric type.

18. The method according to claim 1, wherein a numerical count of the multiple predetermined material types is countably small.

19. The method according to claim 1, further comprising providing a candidate material type identity for the unknown material based on the assigned probabilities of the material types.

20. An apparatus for classifying the material type of an unknown material into a probability distribution of multiple predetermined material types by using a collection of plural predetermined material classifiers, wherein each material type of the multiple predetermined material types is associated with a corresponding best performing classifier from the collection of plural predetermined material classifiers by a predesignated stored association, the apparatus comprising:

an application unit configured to apply the plural material classifiers to the unknown material to obtain a list of candidate material types;

a look up unit configured to look up a list of potential best performing classifiers using the list of candidate material types as a reference into the predesignated stored association; and an assigning unit configured to assign a respective probability that the unknown material belongs to a material type based on the list of potential best performing classifiers, wherein the application unit is further configured to obtain one or more feature vectors for the unknown material and to input a corresponding one of the feature vectors into each of the plural material classifiers so as to obtain an output representative of material type from each of the plural material classifiers, and wherein each of the application unit, the look up unit and the assigning unit is implemented using a processor.

21. The apparatus according to claim 20, wherein the output of each material classifier is indicative of a probability that the unknown material belongs to each material type.

22. The apparatus according to claim 20, wherein the output of each material classifier identifies a candidate material type that the unknown material belongs to.

23. The apparatus according to claim 20, wherein the collection of plural material classifiers includes a classifier based on texture discrimination, and the corresponding feature vector for such classifier is representative of texture of the unknown material.

24. The apparatus according to claim 20, wherein the collection of plural material classifiers includes a classifier based on a spectral signature, and the corresponding feature vector for such classifier is representative of spectral reflectance of the unknown material.

25. The apparatus according to claim 20, wherein the collection of plural material classifiers includes a classifier based on a bidirectional reflectance distribution function, and the corresponding feature vector for such classifier is representative of an angular dependence of reflectance of the unknown material.

26. The apparatus according to claim 20, wherein the collection of plural material classifiers includes a classifier based on a bidirectional surface scattering reflectance distribution function, and the corresponding feature vector for such classifier is representative of a subsurface scattering property of the unknown material.

27. The apparatus according to claim 20, wherein the assigning unit is further configured to:

determine a weight for each of the plural predetermined material classifiers by using the list of potential best performing classifiers; and assign a respective probability that the unknown material belongs to a material type based on the weights of the plural predetermined material classifiers.

28. The apparatus according to claim 27, wherein determining a weight for each of the plural predetermined material classifiers comprises a look up from a pre-computed table of weights.

29. The apparatus according to claim 27, wherein determining a weight for each of the plural predetermined material classifiers comprises using a state machine that describes the behavior of the plural predetermined material classifiers, and finding a limit cycle of the state machine.

30. The apparatus according to claim 27, wherein assigning a respective probability that the unknown material belongs to a material type based on the weights of the plural predetermined material classifiers comprises calculating a weighted combination of the plural predetermined material classifiers using the weights.

31. The apparatus according to claim 20, wherein the predesignated stored association by which each material type is associated with a corresponding best performing classifier is based on empirical data from labeled test samples.

32. The apparatus according to claim 20, wherein the predesignated stored association by which each material type is associated with a corresponding best performing classifier is based on theoretical behavior of the classifiers on the material types.

33. The apparatus according to claim 20, wherein the predesignated stored association by which each material type is associated with a corresponding best performing classifier is stored in a look up table.

34. The apparatus according to claim 20, wherein the multiple predetermined material types includes a plastic type.

35. The apparatus according to claim 20, wherein the multiple predetermined material types includes a metal type.

36. The apparatus according to claim 20, wherein the multiple predetermined material types includes a fabric type.

37. The apparatus according to claim 20, wherein a numerical count of the multiple predetermined material types is countably small.

38. The apparatus according to claim 20, further comprising an identification unit configured to provide a candidate material type identity for the unknown material based on the assigned probabilities of the material types.

39. A non-transitory computer-readable storage medium storing a program for causing a computer to implement a method for classifying the material type of an unknown material into a probability distribution of multiple predetermined material types by using a collection of plural predetermined material classifiers, wherein each material type of the multiple predetermined material types is associated with a corresponding best performing classifier from the collection of plural predetermined material classifiers by a predesignated stored association, the method comprising the steps of:

applying the plural material classifiers to the unknown material to obtain a list of candidate material types;

looking up a list of potential best performing classifiers using the list of candidate material types as a reference into the predesignated stored association; and assigning a respective probability that the unknown material belongs to a material type based on the list of potential best performing classifiers, wherein applying comprises obtaining one or more feature vectors for the unknown material and inputting a corresponding one of the feature vectors into each of the plural material classifiers so as to obtain an output representative of material type from each of the plural material classifiers.

\* \* \* \* \*